US007235552B1

(12) United States Patent
Hesse et al.

(10) Patent No.: US 7,235,552 B1
(45) Date of Patent: Jun. 26, 2007

(54) CHOLENIC ACID AMIDES AND PHARMACEUTICAL COMPOSITIONS THEREOF

(75) Inventors: Robert Henry Hesse, Winchester, MA (US); Sundara Katugam Srinivasasetty Setty, Cambridge, MA (US); Malathi Ramgopal, Andover, MA (US)

(73) Assignee: Research Institute for Medicine and Chemistry, Inc., Cambridge, MA (US)

( * ) Notice: Subject to any disclaimer, the term of this patent is extended or adjusted under 35 U.S.C. 154(b) by 984 days.

(21) Appl. No.: 09/630,546

(22) Filed: Aug. 1, 2000

Related U.S. Application Data

(63) Continuation of application No. PCT/GB99/00681, filed on Mar. 8, 1999.

(30) Foreign Application Priority Data

Mar. 6, 1998 (GB) ................................. 9804861.4

(51) Int. Cl.
*A61K 31/535* (2006.01)
*C07J 43/00* (2006.01)
*C07D 295/00* (2006.01)

(52) U.S. Cl. ............................... 514/237.8; 514/231.2; 544/99; 544/106; 540/98; 540/99

(58) Field of Classification Search ............. 514/222.2, 514/231.5, 277, 315, 351, 361, 359, 396, 514/183, 228.8, 231.2, 237.5, 172, 177, 178, 514/237.8; 552/502, 540, 544; 540/107, 540/108, 109, 110, 98, 99; 544/99, 106
See application file for complete search history.

(56) References Cited

U.S. PATENT DOCUMENTS

| 3,291,690 | A |  | 12/1966 | Bertin et al. |  |
| 4,172,076 | A | * | 10/1979 | Hirsch et al. | ................ 540/110 |
| 4,217,288 | A |  | 8/1980 | Deluca et al. | ............. 260/397.2 |

FOREIGN PATENT DOCUMENTS

| DE | 28 14 347 | A |  | 10/1978 |
| EP | 0 562 849 | A |  | 9/1993 |
| EP | 0 619 304 | A |  | 10/1994 |
| FR | 1 512 326 | A |  | 4/1968 |
| GB | 2021115 |  | * | 11/1979 |
| WO | 0 200 859 | A |  | 11/1986 |
| WO | WO 93 09093 | A |  | 5/1993 |
| WO | WO 94 26707 | A |  | 11/1994 |
| WO | WO 9742215 | A1 | * | 11/1997 |
| WO | WO 98 32444 | A |  | 7/1998 |

OTHER PUBLICATIONS

Iwasaki, Shigeo (DN 87:23607, HCAPLUS, abstract of Helv. Chem. Acta (1976), 59(8), 2753-64).*
DeLuca et al. (DN 90:87748, HCAPLUS, abstract of DE 2812741).*
Shigeo Iwasaki; Photochemical Reactions. Part 92.; 1976, Helvetica Chimica Acta, 59(8), 2753-64.*
Sheets J.J. et al., "Active site-directed inhibitors of cytochrome P-450scc. Structural and mechanistic implications of a side chain-substituted series of amino-steroids" J. of Biol. Chem., 1983, XP002104638.
Murato K. et al., "Photochemical reactions. Part 108. Photochemistry of N-acylazoles. VI. Photoreactivities of 1-acyl-1,2,4-triazoles and of 2-acyltetrazoles", Helvetica Chimica Acta., 1980, XP002104639.
Chemical Abstracts, Jun. 21, 1982, Sklar L. A. et al., "Fluorescent cholesteryl esters in the core of low density lipoprotein", 1982, XP002104646.
Iwasaki S., "Photochemical reactions. Part 92. Photochemistry of imidazolides. II. C2-C3 cleavage of carboxylic acid chains. A convenient new method for the side-chain degradation of bile acids and of lanosterol", Helvetica Chimica Acta., 1976, XP002104640.
D.F. Louw et al., "Delta-5-Steroids and Provitamins D with Branched Side Chains. III. Preparation and Reduction of Some delta-5-Steroid-omega-amides", Recueil Des Travaux Chimiques Des Pays-Bas., 1954, XP002104641.
R.H. Levin et al., "Steroid Acids and their Transformation Products. IV. Epimeric 24-Phenyl-5-cholen-3(beta),24-diols and Related Compounds", J. Amer. Chem. Soc., 1948, XP002104642.
A.F. Chaplin et al., "The Steroid Series. Part IV. Some Basic Derivatives", J. of Chem. Soc., 1959, XP002104643.
Ruan B. et al., "An alternative synthesis of 4,4-Dimethyl-5alpha-cholesta-8,14,24-trien-3beta-ol, an intermediate in sterol biosynthesis and a reported activator of meiosis and of nuclear orphan receptor LXRalpha", Bioorgan. & Med. Chem. Letters., 1998, XP004136854.

(Continued)

*Primary Examiner*—Sabiha N. Qazi
(74) *Attorney, Agent, or Firm*—Bacon & Thomas PLLC

(57) ABSTRACT

Novel sterol derivatives of formula (I), in which: $R^1$ represents a hydroxyl group or protected hydroxyl group, $R^2$ represents a hydrogen atom and a double bond is present at c, or $R^1$ and $R^2$ together represent an oxo group and a double bond is present at b or double bonds are present at a and b; $R^3$ represents a methyl group having α- or β-configuration; $R^4$ and $R^5$, which may be the same or different, are selected from hydrogen atoms and aliphatic, cycloaliphatic, araliphatic and aryl groups, or together with the nitrogen atom to which they are attached form a heterocyclic group; and X represents a polymethylene group containing 2–5 carbon atoms, an oxa group-containing analogue thereof in which a methylene group other than that attached to the —CO.NR$^4$R$^5$ moiety is replaced by an oxygen atom, or an unsaturated analogue thereof containing up to two double bonds. Active compounds of the invention exhibit potent effects on the modulation of cell growth and differentiation and possess an advantageous therapeutic ratio by virtue of their low levels of calcaemic activity.

4 Claims, No Drawings

OTHER PUBLICATIONS

Janowski, Bethany A. et al., "An oxysterol signalling pathway mediated by the nuclear receptor LXR.alpha.", Nature, 1996, XP002104644.

Janowski, Bethany A. et al., "Structural requirements of ligands for the oxysterol liver X receptors LXR.alpha. And LXR.beta." Proc. of Nat'l Acad. of Sciences of USA, 1999, XP002104645.

* cited by examiner

CHOLENIC ACID AMIDES AND PHARMACEUTICAL COMPOSITIONS THEREOF

This application is a continuation of co-pending international application number PCT/GB99/00681, filed Mar. 8, 1999 (of which the entire disclosure of the pending, prior application is hereby incorporated by reference).

This invention relates to novel sterol derivatives, more particularly to sterol derivatives in which the 17-position side chain terminates in an amide group and which exhibit cell modulating activity.

It is well known that 9,10-seco sterol derivatives such as vitamin $D_3$ play a vital role in the metabolism of calcium by promoting intestinal absorption of calcium and phosphorus, maintaining adequate serum levels of calcium and phosphorus, and stimulating mobilisation of calcium from the bone fluid compartment in the presence of parathyroid hormone. Following the discovery that D vitamins are hydroxylated in vivo, at the 25-position in the liver and at the 1α-position in the kidneys, and that the resulting 1α,25-dihydroxy metabolite is the biologically active material, extensive studies have been carried out on vitamin D analogues hydroxylated at, for example, the 1α- and 24R- or 25-positions.

The natural metabolite 1α,25-dihydroxy vitamin $D_3$ has additionally been found to have effects on cellular metabolism, these cell modulating effects including stimulation of cell maturation and differentiation, immunosuppressive effects and immunopotentiating effects (e.g. by stimulating the production of bactericidal oxygen metabolites and the chemotactic response of leukocytes). However, the potent effects of compounds such as 1α,25-dihydroxy vitamin $D_3$ on calcium metabolism will normally preclude their use in this area, since doses sufficient to elicit a desired cell modulating effect will tend to lead to unacceptable hypercalcaemia.

This has led to attempts to synthesize new vitamin D analogues which have reduced effects on calcium metabolism but which still exhibit the desired effects on cellular metabolism. Representative examples of such analogues, together with summaries of earlier attempts to solve this problem, are given in WO-A-9309093, WO-A-9426707 and WO-A-9525718, the contents of which are incorporated herein by reference.

It is currently believed that such vitamin D analogues act as general regulators of cell growth and differentiation through receptor-mediated (especially nuclear receptor-mediated) processes involving modulation of vitamin D responsive genes (M. R. Waters, Endoc. Rev. 13, pp. 719–764 [1992]). It has also hitherto been assumed that the seco steroid 5,7,10(19)-triene system or a similar 19-nor seco steroid 5,7-diene system is a prerequisite for any form of cell modulating activity. Thus, whilst workers investigating vitamin D analogues have modified the A-ring and 17-position side chain and in certain cases have made more drastic modifications to the overall molecular skeleton such as modification or even elimination of the C- and/or D-rings, they have attempted to retain the triene or conjugated diene system (Gui-Dong Zhu et al., Bioorganic & Med. Chem. Lett. 6, pp. 1703–1708 [1996]; K. Sabbe et al., Bioorganic & Med. Chem. Lett. 6, pp. 1697–1702 [1996]).

Workers have recently reported the observation of non-genomic rapid responses to vitamin D analogues which they attribute to interaction with a putative cell membrane-located vitamin D receptor (A. W. Norman et al., J. Steroid Biochem. and Mol. Biol. 56, pp. 13–22 [1996]). It has also been reported that such non-genomic rapid effects may be elicited by 1α,3β,25-trihydroxycholesta-5,7-diene, i.e. the pro-vitamin form of 1α,25-dihydroxy vitamin $D_3$, which is not a seco steroid; this has been attributed to the ability of the pro-vitamin to mimic the 6,7-s-cis conformation of the normal vitamin D triene (Norman, op. cit.). However, the pro-vitamin has been reported to have little ability to elicit the genomic effect believed to underlie modulation of cell growth and differentiation (Norman, op. cit.) and has also been reported not to exhibit the typical effects of vitamin D on skin (R. Gniadecki et al., British J. Dermatol. 132, pp. 841–852 [1995]).

The present invention is based on the surprising finding that a range of simple sterol derivatives which have an intact tetracyclic nucleus and thus lack both the seco steroid triene system of vitamin D analogues and the ability to mimic a conjugated conformational isomer thereof, exhibit potent effects on the modulation of cell growth and differentiation as estimated by their ability to inhibit growth and promote differentiation of a variety of cancer cell lines. The compounds possess an advantageous therapeutic ratio by virtue of their low levels of calcaemic activity, for example as determined by their effects on serum calcium and phosphorus levels in rats.

The compounds of the invention comprise 3β-sterols (and O-protected derivatives thereof) having a double bond at the 5(6)-position and an amide-terminated 17-position side chain, as well as corresponding 17-substituted steroid-3-ones having 4-ene or 1,4-diene double bonds.

Thus according to one embodiment of the invention there are provided compounds of formula (I)

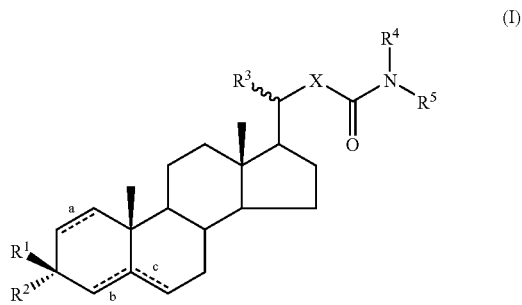

in which:

$R^1$ represents a hydroxyl group or protected hydroxyl group, $R^2$ represents a hydrogen atom and a double bond is present at c, or $R^1$ and $R^2$ together represent an oxo group and a double bond is present at b or double bonds are present at a and b;

$R^3$ represents a methyl group having α- or β-configuration;

$R^4$ and $R^5$, which may be the same or different, are selected from hydrogen atoms and aliphatic, cycloaliphatic, araliphatic and aryl groups, or together with the nitrogen atom to which they are attached form a heterocyclic group; and X represents a polymethylene group containing 2–5 carbon atoms, an oxa group-containing analogue thereof in which a methylene group other than that attached to the —CO.NR$^4$R$^5$ moiety is replaced by an oxygen atom, or an unsaturated analogue thereof containing up to two double bonds.

Where $R^1$ represents a protected hydroxyl group this may, for example, comprise any suitable cleavable O-protecting group such as is commonly known in the art. Representative groups include (i) etherifying groups such as silyl groups (e.g. tri(lower alkyl)silyl groups such as trimethylsilyl, triethylsilyl, triisopropylsilyl or t-butyldimethylsilyl; tri(aryl) silyl groups such as triphenylsilyl; and mixed alkyl-arylsilyl groups), lower (e.g. $C_{1-6}$) alkyl groups optionally interrupted by an oxygen atom (e.g. such as methyl, methoxymethyl or methoxyethoxymethyl) and cyclic ether groups (e.g. such as tetrahydropyranyl), and (ii) esterifying groups such as lower (e.g. $C_{1-6}$) alkanoyl (e.g. such as acetyl, propionyl, isobutyryl or pivaloyl), aroyl (e.g. containing 7–15 carbon atoms, such as benzoyl or 4-phenylazobenzoyl), lower (e.g. $C_{1-6}$) alkane sulphonyl (e.g. such as methane sulphonyl or halogenated methane sulphonyl) and arene sulphonyl (e.g. such as p-toluene sulphonyl).

Such O-protected derivatives of compounds of formula (I) are useful in the preparation of active compounds (I) in which $R^1$ represents a hydroxy group and may also, where the O-protecting group is metabolically labile in vivo, be useful directly in therapy.

Where $R^3$ in formula (I) is a methyl group in the α-configuration the compounds have the 20R configuration characteristic of natural sterols such as cholesterol; where $R^3$ is in the β-configuration the compounds have the 20S configuration of the corresponding epi-derivatives. It will be appreciated that the invention also embraces mixtures of the two isomers.

Aliphatic groups represented by $R^4$ and $R^5$ may, for example, include lower (e.g. $C_{1-6}$) alkyl groups such as methyl, ethyl, propyl and butyl groups. Cycloaliphatic groups may, for example, include lower (e.g. $C_{3-8}$) cycloalkyl groups such as cyclopropyl, cyclopentyl and cyclohexyl groups. Araliphatic groups may, for example, include $C_{6-12}$ aryl-$C_{1-4}$ alkyl groups such as benzyl or phenethyl. Aryl groups may, for example, include $C_{6-12}$ carbocyclic aryl groups such as phenyl or naphthyl, optionally carrying one or more substituents, for example selected from halo (e.g. chloro or bromo), lower (e.g. $C_{1-4}$) alkyl such as methyl, lower (e.g. $C_{1-4}$) alkoxy such as methoxy, lower (e.g. $C_{2-4}$) alkanoyl such as acetyl, lower (e.g. $C_{1-4}$) alkylamino or dialkylamino such as methylamino or dimethylamino, nitro, carbamoyl and lower (e.g. $C_{2-4}$) alkanoylamino such as acetamido.

Where the group $R^4R^5N$— represents a heterocyclic group this will typically contain at least one heteroatom selected from O, N and S, and may comprise one or more rings, e.g. each having 5 or 6 ring members. Representative heterocyclic $R^4R^5N$— groups thus include N-attached pyrrolyl, pyrazolyl, imidazolyl, indolyl, indazolyl, purinyl, pyrrolindinyl, imidazolidinyl, pyrazolidinyl, piperidinyl, morpholino, thiazolidinyl and thiamorpholino.

The group X may, for example, be represented by the formula —$CH_2$—$(CH=CH)_m$—$(CH_2)_n$— where m is 0, 1 or 2 and n is 0 or an integer such that 2m+n=1, 2, 3 or 4. Alternatively X may be a group of formula —$(CH_2)_p$—O—$(CH_2)_q$— where p is 0, 1, 2 or 3, q is 1, 2, 3 or 4 and p+q does not exceed 4.

The cell modulating activity of compounds according to the invention, including O-protected derivatives in which the O-protecting group is metabolically labile, combined with their substantial lack of calcaemic effect, render them of interest both alone and as adjuncts in the management of neoplastic disease, particularly myelogenous leukemias as well as neoplastic disease of the brain, breast, stomach, gastrointestinal tract, prostate, pancreas, uro-genital tract (male and female) and pulmonary neoplasia. Their ability to promote closure of mouse ear punches suggests their use, either alone or as adjuncts, as agents to promote wound healing. They may also be useful, either alone or as adjuncts, in the chemotherapy of infection and in other therapeutic modalities in which mononuclear phagocytes are involved, for example in treatment of bone disease (e.g. osteoporosis, osteopenia and osteodystrophy as in rickets or renal osteodystrophy), autoimmune disease, host-graft reaction, transplant rejection, inflammatory diseases (including modulation of immunoinflammatory reactions), neoplasias and hyperplasias, myophathy, enteropathy and spondylitic heart disease. Additionally, they may be useful in suppression of parathyroid hormone (e.g. as in serum calcium homeostasis), in treatment of dermatological diseases (for example including acne, alopecia, eczema, pruritus, psoriasis and skin aging, including photoaging), hypertension, rheumatoid arthritis, psoriatic arthritis, secondary hyperparathyroidism, asthma, cognitive impairment and senile dementia (including Alzheimer's disease), in fertility control in both human and animal subjects, and in management of disorders involving blood clotting (e.g. by dissolution of existing clots and/or by prevention of clotting). The invention embraces use of these compounds in the therapy or prophylaxis of such conditions and in the manufacture of medicaments for use in such treatment or prophylaxis.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 0.2–2500 μg, e.g. 0.4–500 μg, of active compound according to the invention per unit dosage form. The compositions may if desired incorporate one or more further active ingredients.

A suitable daily dose of an active compound according to the invention may for example be in the range 0.4–5000 μg, e.g. 0.8–1000 μg, per day, depending on factors such as the severity of the condition being treated and the age, weight and condition of the subject.

Compounds according to the invention may be prepared by any convenient method, for example by reaction of a compound containing a precursor for the desired side chain in one or more stages and with one or more reactants serving to form the desired 17-position side chain, followed if necessary and/or desired by removal of any O-protecting group, oxidation of a 3β-ol to a 3-one and consequent isomerisation of a 5(6)-ene to a 4-ene, and oxidation to form a 1,4-diene.

Appropriate techniques for formation of a desired side chain include those described in the aforementioned WO-A-9309093 and WO-A-9426707.

By way of example, compounds of formula (I) in which X is a group —$CH_2$—$(CH=CH)_n$—$(CH_2)$— as hereinbefore defined may be prepared by appropriate reaction of a compound of formula (II)

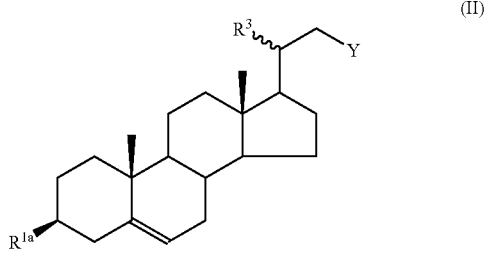

(II)

in which:

$R^{1a}$ represents a protected hydroxyl group, $R^3$ is as hereinbefore defined, and Y represents an oxo or phosphoranylidene group; a metallated silane or sulphone group; a group —$(CH_2)_xL$ where x is 0, 1 or 2 and L represents a leaving group (e.g. a sulphonate ester group such as lower alkyl, sulphonyloxy, lower fluoroalkyl sulphonyloxy or aryl sulphonyloxy, or a halogen atom such as chlorine, bromine or iodine); or a group —$(CH_2)_yR^6$ where y is 0, 1, 2 or 3 and $R^6$ represents a cyano group or an esterified carboxyl or thiocarboxyl group (e.g. an alkoxycarbonyl, aralkoxycarbonyl, aryloxycarbonyl, alkylthiocarbonyl, aralkylthiocarbonyl or arylthiocarbonyl group).

Reactions which may be used to prepare compounds of formula (I) in which X represents a polymethylene group (i.e. where m=0) include:—

(1) Reaction of a compound of formula (II) in which Y represents a group —$(CH_2)_xL$ as hereinbefore defined with a metallated or dimetallated salt of an amide of formula (III)

$$CH_3.CO.NR^4R^5 \quad (III)$$

(where $R^4$ and $R^5$ are as hereinbefore defined). Representative salts include alkali metal salts such as lithium salts and may be prepared by reaction with a base such as lithium diisopropylamide.

(2) Reaction of a compound of formula (III) in which Y represents a group —$(CH_2)_yR^6$ as hereinbefore defined to convert the ester, thioester or cyano group $R^6$ to the desired amide group, e.g. directly by aminolysis of an ester or thioester or indirectly via the corresponding free acid obtained by hydrolysis of the ester, thioester or nitrile or via an acid halide obtained therefrom. It will be appreciated that nitrites of formula (II) may be partially hydrolysed so as directly to yield compounds (I) in which $R^4$ and $R^5$ are hydrogen atoms.

(3) Reaction of a compound of formula (II) in which Y represents a group —$(CH_2)_xL$ as hereinbefore defined with a reagent such as a metal cyanide or metallated trithiane which is capable of introducing a one carbon fragment, and conversion of the group so introduced into the desired —$CO.NR^4R^5$ group, for example as described for process (2).

Reactions which may be used to prepare compounds of formula (I) in which X is unsaturated (i.e. where m=1 or 2) include:—

(4) Reaction of a compound of formula (II) in which Y represents an oxo group according to a Wittig type reaction, for example with a phosphorane of formula (IV)

$$(R^h)_3P=CH-(X^1)_z-R^c \quad (IV)$$

where $X^1$ is an alkylene or alkenylene group containing up to 2 carbon atoms; z is 0 or 1; $R^h$ is a hydrocarbyl group (e.g. an alkyl or aralkyl group or an aryl group such as phenyl); and $R^c$ is the carbamoyl group —$CO.NR^4R^5$ as hereinbefore defined or a precursor group convertible thereto (e.g. an ester, thioester or cyano group). Where $R^c$ represents a precursor group, the reaction is followed by conversion to generate the group —$CO.NR^4R^5$, for example as described for process (2). Alternatively the phosphorane (IV) may be replaced by a metallated silane (V)

$$(R^h)_3Si-CHM-(X^1)_z-R^c \quad (V)$$

or a metallated sulphone (VI)

$$R^hSO_2-CHM-(X^1)_z-R^c \quad (VI)$$

where $X^1$, z, $R^h$ and $R^c$ are as hereinbefore defined and M represents a metal atom (e.g. an alkali metal such as lithium or sodium). In this last case the reaction is immediately followed by reduction of the intermediate hydroxysulphone to form the required double bond, for example using sodium amalgam. It will be appreciated that reactions of this type may also be effected using a compound of formula (II) in which Y is a phosphoranylidene group =$P(R^h)_3$ or a metallated derivative of a compound (II) in which Y is —$Si(R^h)_3$ or —$SO_2R^h$ with an aldehyde of formula (VII)

$$OHC-(X^1)_z-R^c \quad (VII)$$

($R^h$, $X^1$, z and $R^c$ having the above-defined meanings).

Compounds of formula (I) wherein X is a group $-(CH_2)_p-O-(CH_2)_q-$ as hereinbefore defined may, for example, be prepared by:—

(5) Reaction of a compound of formula (VIII)

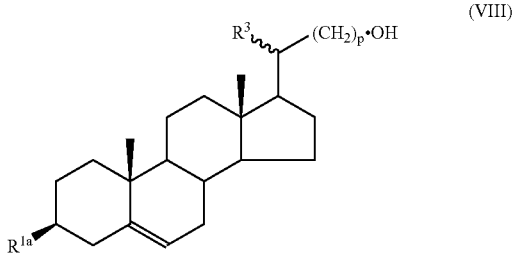

(where $R^{1a}$, $R^3$ and p are as hereinbefore defined) with a compound of formula (IX)

$$L.(CH_2)_q.R^c \quad (IX)$$

(where $R^c$, L and q are as hereinbefore defined, L preferably being a halogen atom), followed if necessary by conversion of a precursor group $R^c$ to generate the desired group $-CO.NR^4R^5$, e.g. as described above for process (2).

(6) Reaction of a compound of formula (X)

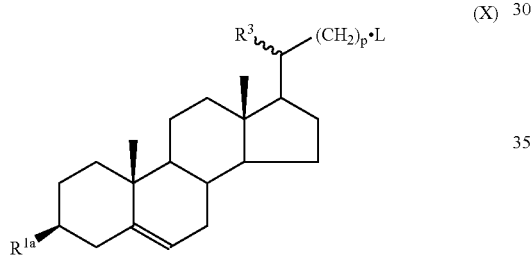

(where $R^{1q}$, $R^3$, L and p are as hereinbefore defined, L preferably being a highly reactive leaving group such as trifluoroacetate, tosylate or trifluoromethane sulphonate) with a compound of formula (XI)

$$HO.(CH_2)_q.R^c \quad (XI)$$

(where $R^c$ and q are as hereinbefore defined), followed if necessary by conversion of a precursor group $R^c$ to generate the desired group $-CO.NR^4, R^5$, e.g. as described above.

(7) Where q is 2, by base catalysed Michael addition of a compound of formula (VIII) as defined above to an acrylate ester, e.g. of formula (XII)

$$CH_2=CH.CO.OR^e \quad (XII)$$

(where $R^e$ is an esterifying group, e.g. a hydrocarbyl group such as a lower alkyl or aryl group), followed by conversion of the ester grouping to the desired group $-CO.NR^4N^5$, e.g. as described above.

Reagents such as compounds of formula (IX) in which $R^c$ is the carbamoyl group $-CO.NR^4R^5$ may, for example, be prepared by reaction of an appropriate ω-haloalkanoyl chloride (e.g. 4-bromobutyryl chloride where it is desired to synthesise a compound of the invention in which q is 3) with an amine $R^4R^5NH$ (where $R^1$ and $R^5$ are as hereinbefore defined). It is convenient to prepare such a reagent in situ, i.e. without subsequent purification, preferably using a molar excess of the amine so as to leave a sufficient excess of base to react with acid liberated in the ensuing coupling reaction with a compound of formula (VIII).

Conversion of the protected hydroxyl group $R^{1a}$ in a product to a hydroxyl group $R^1$ may, for example, be effected by conventional deprotection methods such as are well documented in the literature. Thus an esterifying protecting group may be removed by basic hydrolysis, for example using an alkali metal alkoxide in an alkanol. Etherifying protecting groups such as silyl groups may be removed by acid hydrolysis or by treatment with a fluoride salt, for example a tetraalkylammonium fluoride such as tetrabutylammonium fluoride. It will be appreciated that the use of acid-labile but base-stable silyl protecting groups may be of particular advantage during homologation steps to build up a desired 17-position side chain in view of the strongly basic conditions normally employed for such reactions.

Conversion of 3β-ols of formula (I) to corresponding 3-ones may be effected using any appropriate oxidising agent, e.g. Swern oxidation; the oxidation will normally be accompanied by spontaneous isomerisation to the 4-en-3-one. Where a 1,4-dien-3-one is desired, the additional double bond may, for example, be generated by reaction with selenium dioxide in t-butanol, or by dehydrogenation using 2,3-dichloro-5,6-dicyano-1,4-benzoquinone.

Starting materials of formula (II) in which Y represents oxo may be prepared from known pregnenolones (XIII)

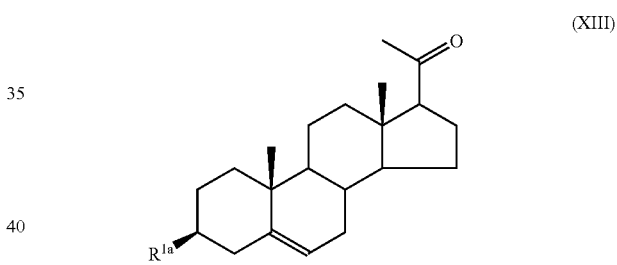

(where $R^{1a}$ is as hereinbefore defined) by Wittig reaction with an alkoxymethylenephosphorane or other one carbon atom alkoxy ylide.

Alternatively, known steroid-5(6)-en-17-ones may be subjected to a Wittig reaction to generate a compound of formula (XIV)

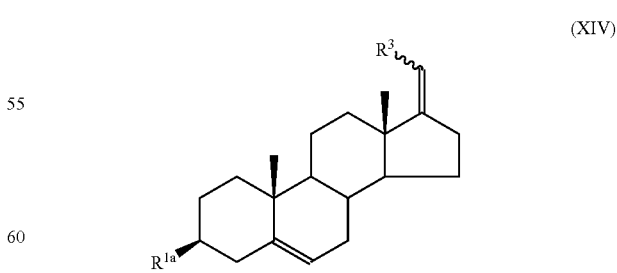

(where $R^{1a}$ and $R^3$ are as hereinbefore defined) which may then be reacted with a dienophile (e.g. formaldehyde or a functional equivalent thereof, or a proparagyl ester) to yield a compound of formula (XV)

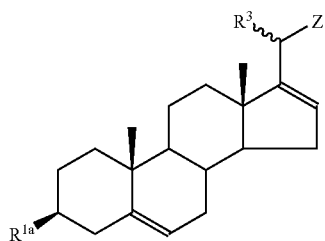

(XV)

(where $R^{1a}$ and $R^3$ are as hereinbefore defined and Z is either —$CH_2OH$ or —$CH{=}CH.CO.OR^h$ where $R^h$ is as hereinbefore defined). Where Z is —$CH_2OH$ this may be converted to a —$CH_2Y$ group, for example, by oxidation to form a compound in which Y is oxo, or by sulphonate ester formation (e.g. tosylation), and preferably also nucleophilic displacement with halide ion, to yield a compound in which Y is —$(CH_2)_xL$ where x is 0. The 16,17-double bond is easily reduced and may be removed by hydrogenation at any appropriate step of the reaction sequence.

Preparation of the above starting materials and other intermediates useful in the preparation of compounds according to the invention is described by Batcho et al., Helv. Chim. Acta. 64, pp. 1682–1687 [1981], Midland et al., Tetrahedron Lett. 23(20), pp. 2077–2080 [1982], Krubiner et al., J. Org. Chem. 31, pp. 24–26 [1965] and Dauben et al., J. Am. Chem. Soc. 103, pp. 237–238 [1980].

The following non-limitative examples serve to illustrate the invention.

Preparation 1

3β-Triisopropylsilyloxypregn-5(6)-ene-20-carboxaldehyde [Formula (II)—$R^{1a}{=}(i{-}Pr)_3SiO$, $R^3{=}CH_3$, Y=O]

A solution of methoxymethyl-triphenylphosphonium chloride (9.87 g) in a mixture of tetrahydrofuran (50 ml) and toluene (50 ml) at 0° C. was treated with lithium diisopropylamide (14.46 ml of a 1.5 M solution in tetrahydrofuran). After 30 minutes 3β-triisopropylsilyloxypregn-5(6)-en-20-one (6.3 g) in toluene (4 ml) followed by a toluene wash (2 ml) were added dropwise, and the resulting mixture was stirred at 0° C. for 1 hour, allowed to warm to room temperature and stored overnight with stirring. The mixture was then treated with ammonium chloride and extracted with ethyl acetate to give the intermediate 20-methoxymethylidene compound, which was purified by chromatography: NMR ($CDCl_3$) δ 0.63 (18-H's), 3.33 ($OCH_3$), 5.6 (6-H).

The above intermediate (all) was taken up in a mixture of acetic acid (54 ml), water (2.4 ml) and tetrahydrofuran (27 ml), treated with p-toluenesulphonic acid (240 mg) and stored overnight with stirring. The product was extracted into ethyl acetate and washed with aqueous sodium bicarbonate, whereafter solvent removal gave the 3-desilylated analogue of the title compound (4.23 g): NMR ($CDCl_3$) δ 0.63, 0.72 (two signals, 18-H's) 1.0 (19,20-H's), 5.23 (6-H), 10.7 (HC=O); IR ($CDCl_3$) $v_{max}$ 1770 cm$^{-1}$.

The desilylated intermediate (all) in methylene chloride (8.5 ml) containing imidazole (2.415 g) was treated with triisopropylsilyl chloride (1.86 ml), and the resulting mixture was stored overnight at room temperature with stirring.

The product was extracted into ethyl acetate, washed with water and isolated by column chromatography to give the title compound.

Preparation 2

20α- and 20β-hydroxymethyl-3β-triisopropylsilyloxypregn-5(6)-ene [Formula (II)—$R^{1a}{=}(i{-}Pr)_3SiO$, $R^3{=}CH_3$, Y=OH]

A solution of the 20-carboxaldehyde from Preparation 1 (1.2 g) in a mixture of methanol (12 ml) and benzene (1.2 ml) was treated with sodium borohydride (800 mg), stirred at room temperature for 1 hour, cooled, treated with ammonium chloride and extracted with ethyl acetate. Solvent removal from the extract afforded the title compounds, which were resolved by chromatography into less polar and more polar isomers, tentatively assigned the 20α- and 20β-configurations respectively.

Preparation 3

20α-Tosyloxymethyl-3β-triisopropylsilyloxypregn-5(6)-ene [Formula (II)—$R^{1a}{=}(i{-}Pr)_3SiO$, $R^3{=}β{-}CH_3$, Y=OTs]

The more polar alcohol from Preparation 2 (310 mg) in methylene chloride containing pyridine (0.355 ml) was treated with tosyl chloride (243 mg), stirred at room temperature for 3 hours, treated with aqueous sodium bicarbonate and methylene chloride, stirred overnight and treated with 1,8-bisdimethylaminonaphthalene (25 mg). The product was extracted into methylene chloride and the extracts were washed successively with 2% hydrochloric acid, sodium bicarbonate and water, dried and concentrated in vacuo. Chromatography gave the title compound (380 mg).

Preparation 4

20β-Bromomethyl-3β-triisopropylsilyloxypreqn-5(6)-ene [Formula (II)—$R^{1a}{=}(i{-}Pr)_nSiO$, $R^3{=}β{-}CH_3$, Y=Br]

The tosylate from Preparation 3 (380 mg) was dissolved in a mixture of acetonitrile (12 ml) and 1,2-dichloroethane (12 ml) containing 1,8-bisdimethylaminonaphthalene (33 mg), treated with lithium bromide (621 mg) and heated under reflux with stirring for 3 hours. The product was extracted into methylene chloride, washed and purifed by chromatography to give the title compound: NMR ($CDCl_3$) δ 0.66 (18-H's), 5.06 (6-H).

EXAMPLE 1 a) 3β-Triisopropylsilyloxy-20-epi-chol-5(6)-enic acid, piperidine amide [Formula (I)—$R^1{=}(i{-}Pr)_3SiO$, $R^2{=}H$, $R^3{=}β{-}CH_3$, $R^4{+}R^5{=}(CH_2)_5$, $X{=}(CH_2)_2$, double bond at c]

A solution of lithium diisopropylamide (3 ml of a 2M solution in tetrahydrofuran) in tetrahydrofuran (10 ml) was cooled to −78° C. N-Acetylpiperidine (914 mg) in tetrahydrofuran (1 ml and 1 ml wash) was added and the mixture was brought to room temperature for 1 hour and then cooled again to −78° C. Two thirds of the mixture was removed and the bromide from Preparation 4 (107 mg) in tetrahydrofuran (1 ml and 1 ml wash) was added to the remainder. Hexamethylphosphoramide was then added and the resulting mixture was stirred at −78° C. for 1 hour and overnight at room temperature. After treatment with ammonium chloride the product was extracted into ethyl acetate, washed, dried and purified by chromatography to give the title compound (120 mg): NMR (CDCl$_3$) δ 0.63 (18-H's), 3.30–3.2 (m, N—CH$_2$'s), 5.03 (6-H); IR (CDCl$_3$) ν$_{max}$ 1620, 1440 cm$^{-1}$.

b) 3β-Hydroxy-20-epi-chol-5(6)-enic acid, piperidine amide [Formula (I)—R$^1$=OH, R$^2$=H, R$^3$=β-CH$_3$, R$^4$+R$^5$=(CH$_2$)$_5$, X=(CH$_2$)$_2$, double bond at c]

The product from (a) above (120 mg) in tetrahydrofuran (1 ml) was treated with tetrabutylammonium fluoride (1 ml of a 1M solution in tetrahydrofuran) and allowed to stand with stirring at room temperature overnight. The product was extracted into methylene chloride, washed with water and purified by chromatography to give the title compound (88 mg): NMR (CDCl$_3$) δ 0.66 (18-H's), 0.93 (19,21-H's), 1.53 (3–5H's of piperidine ring), 3.26–3.2 (m, N—CH$_2$'s), 5.06 (6-H); IR (CDCl$_3$) ν$_{max}$ 3400, 1620, 1440 cm$^{-1}$.

EXAMPLE 2

3-Oxo-20-epi-chol-4-enic acid, piperidine amide [Formula (I)—R$^1$+R$^2$=O, R$^3$=β-CH$_3$, R$^4$+R$^5$=(CH$_2$)$_5$, X=(CH$_2$)$_2$, double bond at b]

A solution of aluminium isopropoxide (96 mg) in toluene (2.5 ml) was added dropwise to a refluxing solution of the product from Example 1(b) (80 mg) in toluene (4.8 ml) containing cyclohexanone (0.5 ml). Heating was continued for 2 hours, whereafter the mixture was cooled and the product was extracted into ethyl acetate and purified by chromatography to give the title compound (46 mg): NMR (CDCl$_3$) δ 0.66 (18-H's), 0.93 (21-H's), 1.1 (19-H's), 3.63 (m, N—CH$_2$'s), 5.46 (4-H); IR (CDCl$_3$) ν$_{max}$ 1660, 1620, 1440 cm$^{-1}$.

EXAMPLE 3 a) 3β-Triisopropylsilyloxychol-5(6)-enic acid, piperidine amide [Formula (I)—R$^1$=(i-Pr)$_3$SiO, R$^2$=H, R$^3$=α-CH$_3$, R$^4$+R$^5$=(CH$_2$)$_5$, X=(CH$_2$)$_2$, double bond at c]

Treatment of the less polar alcohol from Preparation 2 in accordance with the procedures of Preparations 3 and 4 and Example 1(a) afforded the title compound: NMR (CDCl$_3$) δ 0.66 (18-H's), 3.56 (m, N—CH$_2$'s), 5.03 (6-H); IR (CDCl$_3$) ν$_{max}$ 1620, 1440 cm$^{-1}$.

b) 3β-Hydroxychol-5(6)-enic acid, piperidine amide [Formula (I)—R$^1$=OH, R=H, R$^3$=α-CH$_3$, R$^4$+R$^5$=(CH$_2$)$_5$, X=(CH$_2$)$_2$, double bond at c]

The product from (a) above was treated according to the procedure of Example 1(b) to give the title compound: NMR (CDCl$_3$) δ 0.66 (18-H's), 0.96 (19,21-H's), 1.6 (3–5H's of piperidine ring), 3.3 (m, N—CH$_2$'s), 5.1 (6-H); IR (CDCl$_3$) ν$_{max}$ 3600, 1620, 1440 cm$^{-1}$.

EXAMPLE 4

3-Oxochol-4-enic acid, piperidine amide [Formula (I)—R$^1$+R$^2$=O, R$^3$=α-CH$_3$, R$^4$+R$^5$=(CH$_2$)$_5$, X=(CH$_2$)$_2$, double bond at b]

The product from Example 3(b) was treated according to the procedure of Example 2 to give the title compound: NMR (CDCl$_3$) δ 0.7 (18-H's), 1.1, 1.21 (19,21-H's), 3.26 (m, N—CH$_2$'s), 5.33 (4-H); IR (CDCl$_3$) ν$_{max}$ 1660, 1620 cm$^{-1}$

EXAMPLE 5

3β-Hydroxychol-5(6)-enic acid, morpholine amide [Formula (I)—R$^1$=OH, R$^2$=H, R$^3$=α-CH$_3$, R$^4$+R$^5$=(CH$_2$)$_2$O(CH$_2$)$_2$, X=(CH$_2$)$_2$, double bond at c]

The procedures of Example 3 were repeated, replacing the N-acetylpiperidine in (a) with N-acetylmorphine, to give the title compound: NMR (CDCl$_3$) δ 0.63 (18-H's), 0.96 (19-H's), 3.2–3.7 (m, morpholine-CH$_2$'s), 5.1 (6-H); IR (CDCl$_3$) ν$_{max}$ 3640–3200, 1620, 1430 cm$^{-1}$.

EXAMPLE 6

3-Oxochol-4-enic acid, morpholine amide [Formula (I)—R$^1$+R$^2$=O, R$^3$=α-CH$_3$, R$^4$+R$^5$=(CH$_2$)$_2$O(CH$_2$)$_2$, X=(CH$_2$)$_2$, double bond at b]

The product from Example 5 was treated according to the procedure of Example 2 to give the title compound: NMR (CDCl$_3$) δ 0.66 (18-H's), 3.1–3.7 (m, morpholine-CH$_2$'s) 5.5 (4-H)

EXAMPLE 7

3β-Hydroxychol-5(6)-enic acid, thiamorpholine amide [Formula (I)—R$^1$=OH, R$^2$=H, R$^3$=α-CH$_3$, R$^4$+R$^5$=(CH$_2$)$_2$S(CH$_2$)$_2$, X=(CH$_2$)$_2$, double bond at c]

The procedures of Example 3 were repeated, replacing the N-acetylpiperidine in (a) with N-acetylthiamorphine, to give the title compound: NMR (CDCl$_3$) δ 0.63 (18-H's), 0.93 (19-H's), 2.3–2.7 (m, thiamorpholine-CH$_2$'s), 3.1–3.8 (m, N—CH2's), 5.0–5.3 (b, 6-H); IR (CDCl$_3$) ν$_{max}$ 3640–3100, 1620, 1430 cm$^{-1}$.

EXAMPLE 8

3-Oxochol-4-enic acid, thiamorpholine amide [Formula (I)—R$^1$+R$^2$=O, R$^3$=α-CH$_3$, R$^4$+R$^5$=(CH$_2$)$_2$S(CH$_2$)$_2$, X=(CH$_2$)$_2$, double bond at b]

The product from Example 7 was treated according to the procedure of Example 2 to give the title compound: NMR (CDCl$_3$) δ 0.66 (18-H's), 1.13 (19-H's), 2.3–2.7 (m, thiamorpholine-CH$_2$'s) 3.4–3.9 (m, N—CH$_2$'s), 5.5 (4-H).

EXAMPLE 9

3β-Hydroxychol-5(6)-enic acid, diisopropyl amide [Formula (I)—R$^1$=OH, R$^2$=H, R$^3$=α-CH$_3$, R$^4$+R$^5$=CH(CH$_3$)$_2$, X=(CH$_2$)$_2$, double bond at c]

The procedures of Example 3 were repeated, replacing the N-acetylpiperidine in (a) with N-acetyldiisopropylamine, to give the title compound: NMR (CDCl$_3$) δ 0.63 (18-H's), 0.96 (19-H's), 3.0–3.8 (m, 3-H, N—CH's), 5.0–5.3 (b, 6-H); IR (CDCl$_3$) ν$_{max}$ 3640–3100, 1610, 1440 cm$^{-1}$.

EXAMPLE 10

3-Oxochol-4-enic acid, diisopropyl amide [Formula (I)—R$^1$+R$^2$=O, R$^3$=α-CH$_3$, R$^4$+R$^5$=CH(CH$_3$)$_2$, X=(CH$_2$)$_2$, double bond at b]

The product from Example 9 was treated according to the procedure of Example 2 to give the title compound: NMR (CDCl$_3$) δ 0.7 (18-H's), 1.17 (19-H's), 3.0–4.0 (m, N—CH's), 5.57 (s, 4-H).

EXAMPLE 11

3β-Hydroxy-24,24a-bishomo-chol-5(6)-enic acid, piperidine amide [Formula (I)—R$^1$=OH, R$^2$=H, R$^3$=α-CH$_3$, R$^4$+R$^5$=(CH$_2$)$_5$, X=(CH$_2$)$_4$, double bond at c]

The title compound is prepared from 3β-triisopropylsilyloxychol-5(6)-enic acid by reduction with lithium aluminium hydride followed by the procedures of Example 3.

EXAMPLE 12

3-Oxo-24,24a-bishomo-chol-4-enic acid, piperidine amide [Formula (I)—R$^1$+R$^2$=O, R$^3$=α-CH$_3$, R$^4$+R$^5$=(CH$_2$)$_5$, X=(CH$_2$)$_4$, double bond at c]

The product from Example 11 is treated according to the procedure of Example 2 to give the title compound.

EXAMPLE 13

3β-Hydroxy-20-epi-24-homo-22-oxachol-5(6)-enic acid, piperidine amide [Formula (I)—R$^1$=OH, R$^2$=H, R$^3$=β-CH$_3$, R$^4$+R$^5$=(CH$_2$)$_5$, X=O(CH$_2$)$_2$, double bond at c]

A mixture of 3β-triisopropylsilyloxypregn-5(6)-en-20β-ol (390 mg), ethyl acrylate (2.3 ml), sodium hydroxide (9.2 ml, 50% aqueous), tetrabutylammonium hydroxide (0.038 ml, 40% aqueous solution) and toluene (23 ml) was stirred at room temperature overnight, then diluted with ether and washed with water then brine. The organic portion was concentrated in vacuo and the product (3β-triisopropylsilyloxy-20-epi-24-homo-22-oxachol-5(6)-enic acid, ethyl ester) was isolated by chromatography.

This ester (60 mg) in hexane (6 ml) at −78° C. was treated (dropwise addition) with a solution of piperidyl tin N,N-bistrimethylsilylamide [prepared by reaction of tin bis(N,N-bistrimethylsilylamide) (264 mg) in hexane (6 ml) with piperidine (51 mg)]. The reaction mixture was brought to room temperature, diluted with ethyl acetate, then washed successively with 5M potassium fluoride and brine, dried and concentrated in vacuo. The 3-triisopropylsilyl ether of the title product (20 mg) was isolated by chromatography: NMR (CDCl$_3$) δ 0.63 (18-H's), 3.0–3.9 (m, 3-H, 20-H, —O—CH's, N—CH's), 4.9–5.2 (b, 6-H); IR (CDCl$_3$) ν$_{max}$ 1640, 1470 cm$^{-1}$. Desilylation as in Example 1(b) afforded the title compound: NMR (CDCl$_3$) δ 0.66 (18-H's), 1.0 (19-H's), 3.1–4.0 (m, 3-H, 20-H, —O—CH's, N—CH's), 5.2–5.5 (b, 6-H); IR (CDCl$_3$) ν$_{max}$ 3640–3300, 1620, 1445 cm$^{-1}$.

EXAMPLE 14

3β-Hydroxy-20-epi-22-oxachol-5(6)-enic acid, piperidine amide [Formula (I)—R$^1$=OH, R$^2$=H, R$^3$=β-CH$_3$, R$^4$+R$^5$=(CH$_2$)$_5$, X=O(CH$_2$), double bond at c]

A solution of 18-crown-6 (264 mg) in tetrahydrofuran was added dropwise to a mixture of 3β-triisopropylsilyloxypregn-5(6)-en-20β-ol (474 mg) and potassium hydride (0.3 ml of a 35 wt. % dispersion in mineral oil) in tetrahydrofuran (1 ml). The resulting mixture was stirred for 30 minutes at room temperature, cooled to −10° C., then treated (dropwise addition) with N-α-bromoacetylpiperidine (0.5 ml) in tetrahydrofuran (1 ml). After 30 minutes the reaction mixture was brought to room temperature and allowed to stand overnight. The reaction mixture was then quenched by addition of saturated aqueous ammonium chloride, the products were extracted into ether which was then washed with water and brine, and the solvents were removed in vacuo. The 3-triisopropylsilyl ether of the title product (360 mg) was isolated by chromatography: NMR (CDCl$_3$) δ 0.7 (18-H's), 3.1–3.6 (m, 3-H, 20-H, N—CH's), 3.83 (s, —O—CH$_2$—C=O), 4.9–5.3 (b, 6-H); IR (CDCl$_3$) ν$_{max}$ 1640, 1450 cm$^{-1}$.

Desilylation according to the procedure of Example 1(b) afforded the title compound: NMR (CDCl$_3$) δ 0.7 (18-H's), 1.0 (19-H's), 3.2–3.7 (m, 3-H, 20-H, N—CH's), 3.9–4.1 (d, —O—CH$_2$—C=O), 5.1–5.4 (b, 6-H); IR (CDCl$_3$) ν$_{max}$ 3640–3300, 1640, 1450 cm$^{-1}$.

EXAMPLE 15

3-Oxo-20-epi-22-oxachol-4-enic acid, piperidine amide [Formula (I)—R$^1$+R$^2$=O, R$^3$=β-CH$_3$, R$^4$+R$^5$=(CH$_2$)$_5$, X=O(CH$_2$), double bond at b]

The product from Example 14 was oxidised according to the procedure of Example 2 to afford the title compound: NMR (CDCl$_3$) δ 0.7 (18-H's), 1.1 (19-H's), 3.0–3.5 (m, 3-H, 20-H, N—CH's), 3.7–4.0 (d, —O—CH$_2$—C=O), 5.43 (b, 6-H); IR (CDCl$_3$) ν$_{max}$ 1640, 1450 cm$^{-1}$.

EXAMPLE 16

3β-Hydroxychol-5(6), 22-dienic acid, piperidine amide [Formula (I)—R$^1$=OH, R$^2$=H, R$^3$=α-CH$_3$, R$^4$+R$^5$=(CH$_2$)$_5$, X=CH=CH, double bond at c]

The aldehyde from Preparation 1 is converted into the corresponding 5(6), 22-unsaturated cholenic acid ethyl ester by reaction with the triphenylphosphoranylidene derivateive of ethyl acetate [Formula (IV)—R$^c$=CO.OC$_2$H$_5$, R$^h$=C$_6$H$_5$, z=0], and the latter is in turn converted into the title compound by reaction with the tin reagent of Example 13, followed by desilylation according to the procedure of Example 1(b).

EXAMPLE 17

3-Oxo-20-epi-chol-1.4 dienic acid, piperidine amide [Formula (I)—R$^1$+R$^2$=O, R$^3$=β-CH$_3$, R$^4$+R$^5$=(CH$_2$)$_5$, X=(CH$_2$)$_2$, double bonds at a and b]

The title compound is prepared by dehydrogenating the product from Example 2 with 2,3-dichloro-5,6-dicyano-1,4-benzoquinone.

EXAMPLE 18

3-Oxochol-1,4-dienic acid, piperidine amide [Formula (I)—$R^1+R^2=O$, $R^3=\alpha$-$CH_3$, $R^4+R^5=(CH_2)_5$, $X=(CH_2)_2$, double bonds at a and b]

The title compound is prepared by dehydrogenating the product from Example 4 with 2,3-dichloro-5,6-dicyano-1,4-benzoquinone.

EXAMPLE 19

3β-Hydroxy-20-epi-24-homo-23-oxachol-5(6)-enic acid, piperidine amide [Formula (I)—$R^1=OH$, $R^2=H$, $R^3=\beta$-$CH_3$, $R^4+R^5=(CH_2)_5$, $X=(CH_2)O(CH_2)$, double bond at c]

The title compound is prepared from the more polar product of Preparation 2 by following the procedure of Example 14.

EXAMPLE 20

3-Oxo-20-epi-24-homo-23-oxachol-4-enic acid, piperidine amide [Formula (I)—$R^1+R^2=O$, $R^3=\beta$-$CH_3$, $R^4+R^5=(CH_2)_5$, $X=(CH_2)O(CH_2)$, double bond at b]

The title compound is prepared by oxidation of the product from Example 19 following the procedure of Example 2.

The invention claimed is:

1. Compounds which have a formula (I)

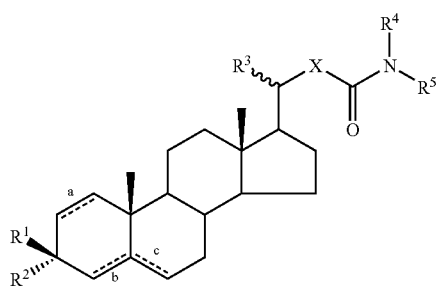

(I)

in which:
  $R^1$ represents a hydroxyl group or a hydroxyl group substituted with a metabolically labile O-protecting group, $R^2$ represents a hydrogen atom and a double bond is present at c, or $R^1$ and $R^2$ together represent an oxo group and a double bond is present at b or double bonds are present at a and b;
  $R^3$ represents a methyl group having α- or β-configuration;
  $R^4$ and $R^5$ together with the nitrogen atom to which they are attached form a morpholino or thiamorpholino group; and
  X represents a group of formula —$CH_2$—$(CH=CH_2)_m$—$(CH_2)_n$— where m is 0, 1 or 2 and n is 0 or an integer such that 2m+n=1, 2, 3 or 4, or a group of formula —$(CH_2)_p$—O—$(CH_2)_q$— where p is 0, 1, 2 or 3, q is 1, 2, 3 or 4 and p+q does not exceed 4, with the proviso that when $R^3$ is α-$CH_3$ and X is $(CH_2)_3$ then $R^4R^5$— is not morpholino.

2. The following compounds:
  3β-hydroxychol-5(6)-enic acid, morpholine amide;
  3-oxochol-4-enic acid, morpholine amide;
  3β-hydroxychol-5(6)-enic acid, thiamorpholine amide; and
  3-oxochol-4-enic acid, thiamorpholine amide.

3. Pharmaceutical compositions comprising a the compound of formula (I)

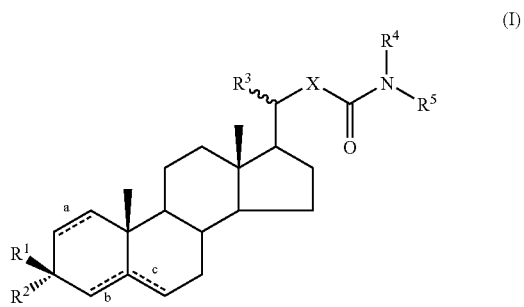

(I)

in which:
  $R^1$ represents a hydroxyl group or a hydroxyl group substituted with a metabolically labile O-protecting group, $R^2$ represents a hydrogen atom and a double bond is present at c, or $R^1$ and $R^2$ together represent an oxo group and a double bond is present at b or double bonds are present at a and b;
  $R^3$ represents a methyl group having α- or β-configuration;
  $R^4$ and $R^5$ together with the nitrogen atom to which they are attached form a morpholino or thiamorpholino group; and
  X represents a group of formula —$CH_2$—$(CH=CH)_m$—$(CH_2)_n$— where m is 0, 1 or 2 and n is 0 or an integer such that 2m+n=1, 2, 3 or 4, or a group of formula —$(CH_2)_p$—O—$(CH_2)_q$— where p is 0, 1, 2 or 3, q is 1, 2, 3 or 4 and p+q does not exceed 4; in admixture with one or more physiologically acceptable carriers or excipients.

4. A pharmaceutical composition as claimed in claim 3 wherein the compounds are selected from the group consisting of:
  3β-hydroxychol-5(6)-enic acid, morpholine amide;
  3-oxochol-4-enic acid, morpholine amide;
  3β-hydroxychol-5(6)-enic acid, thiamorpholine amide; and
  3-oxochol-4-enic acid, thiamorpholine amide.

* * * * *